United States Patent

Vanlerberghe et al.

[11] Patent Number: 5,354,510
[45] Date of Patent: Oct. 11, 1994

[54] USE IN SURFACE-ACTIVE AGENT SOLUTIONS OF AMINOPOLYOL CARBAMATES AS THICKENING AGENTS AND COMPOSITIONS CONTAINING THEM

[75] Inventors: Guy Vanlerberghe, Villevaudé; Claude Mahieu, Paris; Jean L. Morangais, Ozoir la Ferriére, all of France

[73] Assignee: L'Oreal, Paris, France

[21] Appl. No.: 84,156

[22] Filed: Jul. 1, 1993

[30] Foreign Application Priority Data

Jul. 2, 1992 [FR] France .................... 92 08176

[51] Int. Cl.$^5$ .................... C11D 3/32; C11D 1/02; C11D 1/66
[52] U.S. Cl. .................... 252/548; 252/174.21; 252/DIG. 13; 424/70; 560/160
[58] Field of Search .......... 252/548, 174.21; DIG. 13; 560/160; 424/70

[56] References Cited

U.S. PATENT DOCUMENTS

| | | | |
|---|---|---|---|
| 1,927,858 | 12/1931 | Ulrich et al. | 260/106 |
| 2,040,997 | 5/1936 | Johnson | 260/98 |
| 2,184,008 | 12/1939 | Dickey et al. | 28/1 |
| 2,383,737 | 8/1946 | Richardson | 252/152 |
| 2,649,473 | 8/1953 | Chenicek | 260/482 |
| 2,703,798 | 3/1955 | Schwartz | 260/211 |
| 2,808,402 | 10/1957 | Boettner | 260/211 |
| 2,998,445 | 8/1961 | Stewart et al. | 260/482 |
| 4,488,974 | 12/1984 | Keil et al. | 252/8.8 |
| 5,124,079 | 6/1992 | Smid et al. | 252/548 |
| 5,188,769 | 2/1993 | Connor et al. | 252/548 |

FOREIGN PATENT DOCUMENTS

| | | |
|---|---|---|
| 543132 | 12/1955 | Belgium . |
| 0242918 | 10/1987 | European Pat. Off. . |
| 0242919 | 10/1987 | European Pat. Off. . |
| 2379283 | 9/1978 | France . |
| WO92/05764 | 4/1992 | World Int. Prop. O. . |
| 022629 | 12/1992 | World Int. Prop. O. . |

Primary Examiner—Paul Lieberman
Assistant Examiner—Michael P. Tierney
Attorney, Agent, or Firm—Jacobson, Price, Holman & Stern

[57] ABSTRACT

The present invention relates to the use, as thickening agents in surface-active agent solutions, of aminopolyol carbamates corresponding to the general formula:

$$R_1-O-\overset{\overset{\displaystyle O}{\|}}{C}-\underset{\underset{\displaystyle R_2}{|}}{N}-CH_2-(CHOH)_n-CH_2OH \qquad (I)$$

in which:
  $R_1$ represents a linear, saturated $C_8$–$C_3$ alkyl;
  $R_2$ represents hydrogen or a $C_1$–$C_{10}$ alkyl;
  n is between 1 and 5.

The present invention also relates to washing and/or cleaning compositions containing surface-active agents and to these compounds.

19 Claims, No Drawings

USE IN SURFACE-ACTIVE AGENT SOLUTIONS OF AMINOPOLYOL CARBAMATES AS THICKENING AGENTS AND COMPOSITIONS CONTAINING THEM

The invention relates to the use in surface-active agent solutions of aminopolyol carbamates as thickening agents, and to washing and cleaning compositions containing surface-active agents and these compounds.

The structure of the aminopolyol carbamates is already known and described in U.S. Pat. No. 2,040,997.

Research is taking place in the area of the cosmetics industry for washing products having sufficiently thick consistencies so that the detergent compound remains in contact with the body or the hair without flowing as soon as it is applied, in order to prevent its loss and, in the case of shampoos or make-up removers, accidental contact with the eyes. However, the consistency of the washing product must also make it easy to flow from the bottle in which it is contained.

A good washing product must thus have a viscosity such that it flows easily from the bottle but sufficiently slowly on the hair or the body to avoid the abovementioned disadvantages.

Solutions have already been proposed for solving this problem, such as the addition of amphiphilic compounds of specific structures: it concerns fatty acid derivatives, either esterified with polyoxyethylenated chains or amidated with polyhydroxylated amines. One of the most frequently used compounds of this class is the mixture of constituent fatty acids of coconut oil acid amidated with diethanolamine. More recently, it was discovered, in Patent Application EP 285,768, that replacement of diethanolamine by an aminopolyhydroxylated residue deriving from a monosaccharide or polysaccharide, and more precisely the N-methyl-D-glucamine derived from glucose, would improve the thickening of a surface-active agent solution.

As the ideal properties searched for this class of products are to obtain a maximum thickening of the washing product for a reduced amount of additive, up until now a significant amount of electrolyte, such as sodium chloride, combined with the compounds derived from fatty acids in order to enhance their activity, was indispensable for producing satisfactory, but nonetheless restricted, thickenings.

The aim of the present invention is to provide compositions containing surface-active agents which are sufficiently thick without, however, having the abovementioned disadvantages.

It was surprisingly discovered, which forms the subject of the present invention, that replacement of the amide functional group deriving from the fatty acids described above by a carbamate functional group, deriving from fatty alcohols, surprisingly made it possible to improve the thickening of surface-active agent solutions. The surface-active agent solutions containing the carbamates in accordance with the invention have a sufficiently thick consistency even with a minimum amount of additive, especially an electrolyte, while making possible easy flow of the product.

The subject of the present invention is thus the use, in surface-active agent solutions, of aminopolyol carbamates as the thickening agents.

Another subject of the invention consists of a washing and/or cleaning composition containing surface-active agents and, as thickening agent, at least one aminopolyol carbamate.

Other subjects of the invention will become apparent on reading the description and examples which follow.

The compounds used as thickening agents in surface-active agent solutions are aminopolyol carbamates of general formula:

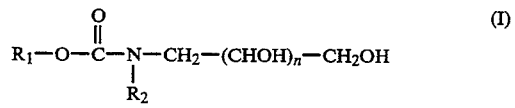

in which:
$R_1$ represents a linear, saturated $C_8$–$C_{13}$ alkyl radical;
$R_2$ represents a hydrogen or a $C_1$–$C_{10}$ alkyl radical;
n is an integer between 1 and 5.

Among the preferred meanings of the substituents defined above, $R_2$ represents $C_1$–$C_6$ alkyl radical and n has the value 4 which corresponds, for the radical

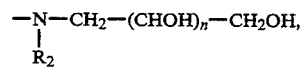

to the aminopolyols themselves derived from a natural monosaccharide such as glucose, galactose, mannose and the like, and more commonly called glucamine, galactamine, mannosamine and the like.

The choice of $R_1$, $R_2$ and n for the aminopolyol carbamate compounds is made according to their solubility in the surface-active solutions concerned.

The more particularly preferred aminopolyol carbamates of general formula (I) are the carbamates of N-methylglucamine, among which there may be mentioned: -N-decyloxycarbonyl-N-methylglucamine.

The aminopolyol carbamates of general formula (I) can be obtained in a number of ways:

They can be prepared by treating the aminopolyol in question, obtained by the reduction in the presence of aqueous ammonia or of primary amines of the corresponding natural monosaccharide, with the linear, saturated $C_8$–$C_{13}$ alkyl chloroformate.

Another process for the preparation of these carbamates which can be used according to the invention consists in reacting a cyclic urethane of an N-alkyl-N-sorbitylcarbamic acid with an alcohol. This process is described in U.S. Pat. No. 2,408,402.

The surface-active agents used in thickened solutions in accordance with the invention can be anionic, nonionic or mixtures of anionic and nonionic surface-active agents.

The anionic surface-active agents which can be used according to the invention are chosen from:

Alkali metal salts, ammonium salts, amine salts, aminoalcohol salts and magnesium salts of the following compounds:
  alkyl sulfates, alkyl ether sulfates, alkylamido ether sulfates, alkyl aryl polyether sulfates, or monoglyceride sulfates;
  alkyl sulfonates, alkylamide sulfonates, alkyl aryl sulfonates, olefin sulfonates, or paraffin sulfonates;
  alkyl sulfosuccinates, alkyl ether sulfosuccinates, or alkylamide sulfosuccinates;
  alkyl sulfosuccinamates;
  alkyl sulfoacetates;
  alkyl phosphates, or alkyl ether phosphates;

acyl sarcosinates, acyl isethionates, or N-acyl taurates.

The alkyl or acyl radical of these various compounds generally consist of a carbon chain containing from 12 to 20 carbon atoms.

There may also be mentioned: salts of fatty acids such as oleic, ricinoleic, palmitic or stearic acids; coconut oil acid or hydrogenated coconut oil acid; acyl lactylates in which the acyl radical contains 8 to carbon atoms.

Among the nonionic surface-active agents, there may more particularly be mentioned: polyethoxylated, polyoxypropylenated or polyglycerolated alcohols, alkylphenols and fatty acids containing fatty chains comprising 8 to 18 carbon atoms, the number of ethylene oxide or propylene oxide groups being between 2 and 50 the number of glycerol groups being between 2 and 30.

There may also be mentioned copolymers of ethylene oxide and of propylene oxide, condensates of ethylene oxide and propylene oxide with fatty alcohols, polyethoxylated fatty amides (preferably containing 2 to 30 moles of ethylene oxide), polyethoxylated fatty amines (preferably from 2 to 30 moles of ethylene oxide), ethanolamides, oxyethylenated (preferably 2 to 30 moles of ethylene oxide) or nonoxyethylenated fatty acid esters of sorbitan, fatty acid esters of polyethylene glycol, phosphoric triesters, fatty acid esters of sucrose, alkylpolyglycosides or fatty amine oxides.

The thickening activity of the aminopolyol carbamates used in accordance with the invention is determined by viscosity measurements at various shear rates using a rheometer operating at a set shear rate.

By these measurements, it was observed that the thickening activity of the aminopolyol carbamates of formula (I) defined above is greater than those of the thickening agents of surface-active agent solution of the prior art.

Another subject of the present invention is washing and/or cleaning compositions containing, in an aqueous medium, surface-active agents and, as thickening agent, at least one aminopolyol carbamate of general formula (I) as defined above.

The aminopolyol carbamate compounds of general formula (I) defined above are present in these compositions in concentrations varying from 0.1 to 40% by weight with respect to the total weight of the composition, and preferably 0.1 to 10% by weight.

The compositions in accordance with the invention also contain, in combination with the aminopolyol carbamate compounds of general formula (I) defined above, electrolytes which make it possible to enhance their activity as thickening agents. Among these electrolytes, there may be mentioned sodium chloride or sodium sulfate.

The electrolytes used in the compositions in accordance with the invention are preferably present in concentrations ranging from 0.01 to 10% by weight with respect to the total weight of the composition.

The surface-active agents are preferably anionic and/or nonionic surface-active agents as defined above.

These surface-active agents are present in the compositions of the present invention in proportions between 1 and 80%, preferably between 1 and 50%, by weight with respect to the total weight of the composition.

The ratio by weight of aminopolyol carbamates of formula (I) defined above to the surface-active agents used in the compositions in accordance with the invention is between 0.05 and 1.

The aqueous medium can consist of water or a mixture of water and organic solvents in order to solubilize the components which would not be sufficiently soluble in water. Among these solvents, there may be mentioned, by way of example, the lower $C_1$–$C_{14}$ alcohols, such as ethanol and isopropanol; glycerol; glycols or glycol ethers such as 2-butoxyethanol, ethylene glycol, propylene glycol and the monoethyl ether and monomethyl ether of diethylene glycol, as well as the aromatic alcohols such as benzyl alcohol or phenoxyethanol, the analogous products and their mixtures.

Other thickening agents different from the aminopolyol carbamates of formula (I) can be added to the compositions in accordance with the invention, such as those chosen from sodium alginate, gum arabic, optionally crosslinked acrylic acid polymers, cellulose derivatives or heterobiopolysaccharides such as xanthan gum. It is also possible to use inorganic thickening agents such as bentonite.

These compositions can also contain other cosmetically acceptable adjuvants such as, for example, sequestering agents, fragrances, buffers, treatment agents, conditioning agents, preserving agents, and the like.

The compositions in accordance with the invention can exist in various forms, such as in the liquid, cream or gel form or any other suitable form, and can be packaged in aerosol containers and in the presence of a propellant in order to form foams.

The pH of the compositions in accordance with the invention varies between 3 and 8. It is adjusted to the value generally used in cosmetics using basifying agents and acidifying agents.

The composition of the invention is used for washing or cleaning keratinous materials, more particularly human keratinous materials, especially hair and skin, after which the latter are rinsed and dried.

The examples which follow are intended to illustrate the invention without, however, having any limiting nature.

EXAMPLE 1

Preparation of (or N-decyloxycarbonyl-N-methylglucamine)

23.4 g of N-methylglucamine (0.12 mole) are dissolved in a mixture of 60 ml of water and 80 ml of tetrahydrofuran in a reactor, and then 40 g of sodium hydrogencarbonate (0.48 mole) are added and dispersed.

While keeping the temperature of the reaction mixture at 20° C., 26.4 g of decyl chloroformate (marketed by SNPE) (0.12 mole) are added dropwise and the mixture is then left for 3 hours with stirring at room temperature and overnight at rest.

The reaction mixture is then filtered (the insoluble product is essentially N-methylglucamine) and the filtrate is cooled at 0° C. overnight. The solid product recovered is recrystallized from 300 ml of acetone (an insoluble material is removed by hot filtration).

After cooling at 0° C. for 12 hours, the crystallized product is recovered and dried. 24 g of pure product are obtained.

Melting point: 59.8° C.

| Elemental analysis: | C | H | N | O |
| --- | --- | --- | --- | --- |
| Theory | 56.97 | 9.83 | 3.69 | 29.51 |
| Found | 56.88 | 9.91 | 3.50 | 29.48 |

COMPOSITION EXAMPLES

EXAMPLE 1: Shampoo

| | |
|---|---|
| Triethanolamine alkyl sulfate ($C_{12}/C_{14}$ 70/30) sold under the name "Empicol TL 40/FL" by the Company Marchon | 30.0 g |
| Compound of Example 1 | 1.33 g |
| Sodium chloride | 1.0 g |
| Preserving agents, fragrance | |
| Water | q.s. for 100.0 g |
| Triethanolamine | q.s. pH 7 |

A clear thickened shampoo is obtained.

EXAMPLE 2: Shower gel

| | |
|---|---|
| Sodium alkyl ether sulfate ($C_{12}/C_{14}$ 70/30) sold under the name "Empicol ESB/3/FL" by the Company Marchon | 80.0 g |
| Compound of Example 1 | 4.0 g |
| Sodium chloride | 3.0 g |
| Preserving agents, fragrance | |
| Water | q.s. for 100.0 g |
| Hydrochloric acid | q.s. pH 7 |

A clear shower gel is obtained.

EXAMPLE 3: Shampoo

| | |
|---|---|
| Alkyl ($C_9/C_{10}/C_{11}$)-20/40/40)-polyglucoside-(1,4) sold under the same APG 300, containing 50% of AM, by the company Henkel | 10 g AM |
| Compound of Example 1 | 7 g |
| Sodium chloride | 5 g |
| Preserving agents, fragrance | q.s. |
| Water | q.s. for 100 g |

We claim:

1. A process for thickening a surface-active agent solution, comprising incorporating into said surface-active agent solution an effective thickening amount of an aminopolyol carbamate of the formula:

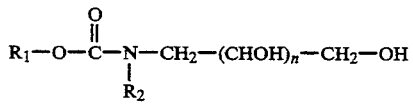

in which:

R₁ represents a linear, saturated $C_8$–$C_{13}$ alkyl radical;
R₂ represents a hydrogen atom or a $C_1$–$C_{10}$ alkyl radical;
n is an integer between 1 and 5; and wherein the surface active agent is different from the aminopolyol carbamate.

2. A process according to claim 1, wherein in the formula (I), R₂ denotes a $C_1$–$C_6$ alkyl radical and n is equal to 4.

3. A process according to claim 1, wherein the aminopolyol carbamate is a carbamate of N-methylglucamine.

4. A process according to claim 1, wherein the carbamate used is N-decyloxy-carbonyl-N-methylglucamine.

5. A process according to claim 1, wherein the surface-active solution comprises a surface-active agent selected from the group consisting of anionic surface-active agents, nonionic surface-active agents and mixtures thereof.

6. A process according to claim 5, wherein the anionic surface-active agents are selected from the group consisting of alkali metal salts, ammonium salts, amine salts, amino-alcohol salts and magnesium salts of the following compounds:

alkyl sulfates, alkyl ether sulfates, alkylamido ether sulfates, alkyl aryl polyether sulfates, and monoglyceride sulfates;

alkyl sulfonates, alkylamide sulfonates, alkyl aryl sulfonates, olefin sulfonates, and paraffin sulfonates;

alkyl sulfosuccinates, alkyl ether sulfosuccinates, and alkylamide sulfosuccinates;

alkyl sulfosuccinamates;

alkyl sulfoacetates;

alkyl phosphates, and alkyl ether phosphates;

acyl sarcosinates, acyl isethionates, and N-acyl taurates; the alkyl and acyl radicals being $C_{12}$–$C_{20}$; fatty acid salts; coconut oil acid and hydrogenated coconut oil acid; and acyl lactylates in which the acyl radical is $C_8$–$C_{20}$.

7. A process according to claim 5, wherein the nonionic surface-active agents are selected from the group consisting of polyethoxylated, polyoxypropylenated and polyglycerolated alcohols, alkylphenols and fatty acids containing fatty chains comprising 8 to 18 carbon atoms; copolymers of ethylene oxide and of propylene oxide, condensates of ethylene oxide and propylene oxide with fatty alcohols, polyethoxylated fatty amides, polyethoxylated fatty amines, ethanolamides, oxyethylenated and nonoxyethylenated fatty acid esters of sorbitan, fatty acid esters of polyethylene glycol, phosphoric triesters, fatty acid esters of sucrose, alkylpolyglycosides and fatty amine oxides.

8. Washing or cleaning composition containing, in an aqueous medium, surface-active agents and at least one aminopolyol carbamate of formula:

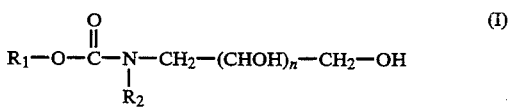

in which:

R₁ represents a linear, saturated $C_8$–$C_{13}$ alkyl radical;
R₂ represents a hydrogen atom or a $C_1$–$C_{10}$ alkyl radical; and
n is an integer between 1 and 5.

9. Composition according to claim 8 which contains surface-active agents selected from the group consisting of anionic surface-active agents, nonionic surface-active agents and mixtures thereof.

10. Composition according to claim 8, wherein the aminopolyol carbamate is present in concentrations varying from 0.1 to 40% by weight with respect to the total weight of the composition.

11. Composition according to claim 8, wherein the surface-active agents are present in concentrations ranging from 1 to 80% by weight with respect to the total weight of the composition.

12. Composition according to claim 11, wherein the surface-active agents are present in concentrations ranging from 1 to 50% by weight with respect to the total weight of the composition.

13. Composition according to claim 8, wherein the ratio by weight of aminopolyol carbamate to the surface-active agents is between 0.05 and 1.

14. Composition according to claim 8, further comprising electrolytes in concentrations ranging from 0.01 to 10% by weight with respect to the total weight of the composition.

15. Composition according to claim 8, further comprising at least one member selected from the group consisting of organic solvents, thickening agents other than the aminopolyol carbamates of formula (I), sequestering agents, fragrances, buffers, treatment agents, conditioning agents, preserving agents.

16. Composition according to claim 8, in a liquid, gel or cream form which is suitable for being packaged in an aerosol container and in the presence of a propellant in order to form foams.

17. Composition according to claim 8, having a pH value between 3 and 8.

18. Process for washing or cleaning keratinous materials, comprising the steps of applying at least one composition as defined in claim 8 to a keratinous material, and then, after an effective amount of exposure time, rinsing said composition off said keratinous material.

19. Composition according to claim 9, wherein the anionic surface-active agents are selected from the group consisting of alkali metal salts, ammonium salts, amine salts, amino-alcohol salts and magnesium salts of the following compounds:

alkyl sulfates, alkyl ether sulfates, alkylamido ether sulfates, alkyl aryl polyether sulfates, and monoglyceride sulfates;

alkyl sulfonates, alkylamide sulfonates, alkyl aryl sulfonates, olefin sulfonates, and paraffin sulfonates;

alkyl sulfosuccinates, alkyl ether sulfosuccinates, and alkylamide sulfosuccinates;

alkyl sulfosuccinamates;

alkyl sulfoacetates;

alkyl phosphates, and alkyl ether phosphates;

acyl sarcosinates, acyl isethionates, and N-acyl taurates;

the alkyl and acyl radicals being $C_{12}$–$C_{20}$; fatty acid salts; coconut oil acid and hydrogenated coconut oil acid; and acyl lactylates in which the acyl radical is $C_8$–$C_{20}$; and the nonionic surface-active agents are selected from the group consisting of polyethoxylated, polyoxypropylenated and polyglycerolated alcohols, alkylphenols and fatty acids containing fatty chains comprising 8 to 18 carbon atoms; copolymers of ethylene oxide and of propylene oxide, condensates of ethylene oxide and propylene oxide with fatty alcohols, polyethoxylated fatty amides, polyethoxylated fatty amines, ethanolamides, oxyethylenated and nonoxyethylenated fatty acid esters of sorbitan, fatty acid esters of polyethylene glycol, phosphoric triesters, fatty acid esters of sucrose, alkylpolyglycosides and fatty amine oxides.

* * * * *